United States Patent [19]
Kubo et al.

[11] Patent Number: 5,827,528
[45] Date of Patent: Oct. 27, 1998

[54] MEDICAL ADHESIVE COMPOSITION

[76] Inventors: Takabumi Kubo, 81-2-202 Naezuka-cho, Souka-shi Saitama; Masatoshi Igarashi, 3-36-1 Chishirodaihigashi Wakaba-ku, Chiba-shi Chiba, both of Japan

[21] Appl. No.: 637,076

[22] Filed: Apr. 24, 1996

[30] Foreign Application Priority Data

Apr. 26, 1995 [JP] Japan ................. 7-125907

[51] Int. Cl.⁶ .............. A61K 9/14; A61L 15/16
[52] U.S. Cl. ................. 424/443; 424/78.08
[58] Field of Search ................. 524/22, 27, 45, 524/54, 55, 71, 274, 419; 424/78.08, 444–449, 77, 484, 486; 523/111, 118; 514/824; 156/334

[56] References Cited

U.S. PATENT DOCUMENTS

| | | | |
|---|---|---|---|
| 4,551,490 | 11/1985 | Doyle et al. | 524/22 |
| 4,775,374 | 10/1988 | Cilento et al. | 604/344 |
| 5,074,852 | 12/1991 | Castellana et al. | 604/336 |

FOREIGN PATENT DOCUMENTS

| | | | |
|---|---|---|---|
| 0512855A2 | 11/1992 | European Pat. Off. | |
| 4185815 | 7/1992 | Japan . | |

*Primary Examiner*—Thurman K. Page
*Assistant Examiner*—Kathryne E. Shelborne
*Attorney, Agent, or Firm*—Haverstock, Garrett & Roberts

[57] ABSTRACT

A medical adhesive composition having as essential components a pressure sensitive adhesive component and a water absorbing component, the pressure sensitive adhesive component consisting of an elastomer comprised of a thermoplastic elastomer and an elastomer having a low compatibility with the thermoplastic elastomer, and a softener containing at least a liquid rubber and a tackifier. The medical adhesive composition has an excellent initial tack, it is subject to little or no cold flow or cracking in storage and in use, has improved flexibility and water absorbing characteristics and swells very little and retains its shape after absorption of water.

6 Claims, No Drawings

MEDICAL ADHESIVE COMPOSITION

INDUSTRIAL FIELD OF UTILIZATION

The present invention relates to a medical adhesive composition which is effective for use in the treatment of wounds, artificially made stomas, naturally formed fistulous openings, and other body openings for disposing of the incontinence of urine or feces, etc., and, in particular, in applications wherein a large amount of exudates or body wastes are excreted from a patient.

BACKGROUND OF THE INVENTION

The following are some of the more important service properties required of a medical adhesive composition:

(a) the medical adhesive composition must readily adhere to a patient's skin by application thereto with a relatively slight force and the composition must have sufficient initial tack that it can be attached to the diseased part of the patient's body without the necessity of applying any unduly large pressure;

(b) the medical adhesive composition must be free from the drawback wherein during use, the adhesive material flows too readily so that the adhesive material can overflow from the base material and stick to the patient's undergarments or other clothing, and the drawback wherein when the medical adhesive composition is applied to a bendable portion of the patient's body the adhesive component is displaced from the body portion as it is bent, such that a crack or a gap in the composition results;

(c) the adhesive composition must have a suitable elasticity and such a flexibility as to be able to follow the movement of the patient's skin;

(d) the medical adhesive composition must have an absorption characteristic and an adhesive characteristic sufficient to enable the composition to absorb sweat that oozes out from the skin and excessive exudates that ooze out from a wound and create a wet state on the wound, yet remain in position under the retention of the adhesion;

(e) the medical adhesive composition must have a shape retention characteristic sufficient to ensure that, even after the composition absorbs the exudates or sweat, it does not get out of shape or swell significantly; and (f) the medical adhesive composition must have such release characteristics that it can be removed without any significant adhesive component remaining on the skin adjacent the wound or diseased body part, and without damage to the skin and/or the wound.

It is also desirable that a medical adhesive composition be gentle to the skin and safe for steady use over a long period of time.

To meet the above requirements and desires, various adhesive compositions each composed in such a manner that a hydrophilic component is incorporated in the adhesive composition have been proposed. Reference for instance, U.S. Pat. No. 4,775,374, corresponding to Japanese Unexamined Patent Application Publication No. Sho 58-103452, which discloses a skin barrier for use by ostomates wherein the adhesive layer comprises a homogeneous blend of one or more pressure sensitive natural or synthetic viscous or elastomeric adhesive substances which can optionally include one or more thermoplastic elastomers, and having dispersed therein one or more water soluble hydrocolloid gums which can optionally include one or more water swellable or inert natural or synthetic fibrous cohesive strengthening agents and other optional ingredients selected from the group consisting of antioxidants, preservatives, and plasticizers. Reference U.S. Pat. No. 4,551,490, corresponding to Japanese Unexamined Patent Application Publication No. Sho 60-20976, which discloses an adhesive composition resistant to biological fluids consisting of a polyisobutylene or a blend of polyisobutylenes and butyl rubber, a styrene radical or block type copolymers, mineral oil, water soluble hydrocolloid gums, water swellable cohesive strengthening agents, and a tackifier. Reference U.S. Pat. No. 5,074,852, corresponding to Japanese Unexamined Patent Application Publication No. Hei 3-92153, which discloses an adhesive layer composition as an occlusive attaching device for ostomy appliances, wherein the occlusive adhesive layers comprise a blend of water soluble or swellable hydrocolloids, and polyisobutylene, or a mixture of polyisobutylenes, or a mixture of polyisobutylenes and non-acrylic elastomers. Reference EP 0512855A2, corresponding to Japanese Unexamined Patent Application Publication No. Hei 5-123389, which discloses an absorbent wound filler composition which comprises at least one of styrene radical or block type copolymers, polyisobutylenes, mineral oil, absorbing powders, and water soluble hydrocolloids. Also reference Japanese Unexamined Patent Application Publication No. Hei 6-200, which discloses a wound protector that comprises a pressure sensitive adhesive, a buffering agent, and an exudate absorbent, wherein the pressure sensitive adhesive comprises a rubber component, an alicyclic saturated hydrocarbon resin, and a liquid rubber.

The above-mentioned medical adhesive compositions can be broadly divided into the following two types. One pertains to compositions each composed in such a manner that, into a polyisobutylene as the base of an elastomer component, a mixture of mineral oil, a hydrocolloid component, and a tackifier are mixed, and, into the resulting composition, a cross-linked rubber, a thermoplastic elastomer, and a cohesive strengthening agent are incorporated for the purpose of making an improvement in respect to cold flow, durability, adhesion, water absorption, etc. The second type pertains to compositions each composed in such a manner that, as an elastomer, a thermoplastic elastomer is used as a base, into which mineral oil, a hydrocolloid component, and a tackifier are added, and, into the resulting composition, a low molecular weight polyisobutylene, a polybutene, a large amount of a tackifier, mineral oil, and a plasticizer, etc. are further incorporated for the purpose of improving initial tack, flexibility, shear adhesion, water absorption, etc.

Drawbacks of the first type of composition include a fast water absorbing speed, and that, after the absorption of water, a disintegration takes place, the tackiness is lost, and so on. On the other hand, the second type of composition has drawbacks such as a slow water absorbing speed, swelling in response to the absorption of water, adhesion that increases with the lapse of time, and injury to the patient's skin or wound when the medical adhesive composition is removed therefrom. Previous attempts at eliminating the drawbacks associated with the first type of composition have included increasing the proportional amount of the elastomer component with respect to the water absorbing component, increasing the proportional amount of the cross-linked rubber component as the elastomer in the pressure sensitive adhesive component, adding a cross-linking agent into the compounding components beforehand so as to effect a cross-linking by the use of irradiation or EB (electron beam) rays, increasing the proportion of non-water absorbing components, and adding a cohesive component, etc. In the case of the second type of composition, reducing the compounding amount of the SIS component, and reducing the compounding amount of the water-absorbing component, etc. have been tried, but have failed to obtain an ideal result. For instance, in the case of the technique of preventing the deformation of the medical adhesive composition as a result of the absorption of water, the water absorption characteristics pertaining to the amount of water absorbed, the water absorbing speed, etc. are deteriorated, and further, a cold flow becomes liable to occur. If the cross-linked component is increased, the initial tack and the water absorption properties have been found to deteriorate, while, if the non-water absorbing component is increased, the medical adhesive composition becomes hardened, thereby lowering its flexibility, and thus, the composition becomes unable to follow the movement of the patient's body and is more prone to cracking. Conversely, in the case of the technique of preventing the occurrence of swelling due to the absorption of water, if the incorporated amount of SIS component and/or cross-linked component are decreased, deformation, cold flow, and cracking are caused. If the water absorbing component is decreased, the water absorbing ability is deteriorated. Thus, the problems pertaining to these antinomic factors have yet to be solved.

OBJECTS OF THE INVENTION

The present invention has been made in view of the above-mentioned drawbacks of the conventional composition and techniques, and it is the object of the invention to provide a medical adhesive composition which has a good initial tack, is relatively free from cold flow and cracking in storage, and in use, has flexibility, good water absorbing characteristics pertaining to the water absorbing speed and the amount of water absorbed, and yet, the deformation of the shape and the swelling of the composition after its absorption of water are very little.

SUMMARY OF THE INVENTION

In order to achieve the above-mentioned object, the preferred medical adhesive composition according to the present invention comprises, as essential components, a pressure sensitive adhesive component and a water absorbing component, the pressure sensitive adhesive component consisting of an elastomer comprised of a thermoplastic elastomer and an elastomer having a low compatibility with the thermoplastic elastomer, and a softener containing at least a liquid rubber and a tackifier.

It is effective to add to the preferred composition according to the present invention a suitable amount of an antioxidant, a suitable amount of a cohesive strengthening agent for improving the cohesion and durability of the composition, or a suitable amount of a hydrophobic component, etc. Further, it is also effective to blend a wound curing promoter, an antimicrobial agent, a germicide, a deodorizer, etc. into the composition.

The medical adhesive composition according to the present invention is excellent in its initial tack and has such a flexibility, in respect of the hardness thereof, as to be able to follow the movement of the patient's skin, is free from cold flow, has an ordinary degree of water absorption and is not subjected to disintegration nor shape deformation; and thus, the composition can be used free from any inconvenience and anxiety.

DETAILED DESCRIPTION OF THE PREFERRED EMBODIMENTS

The present medical adhesive composition comprises a pressure sensitive adhesive component and a water absorbing component as its essential components, the pressure sensitive adhesive component containing an elastomer consisting of a thermoplastic elastomer and an elastomer having a low compatibility with the thermoplastic elastomer, and a softener containing at least a liquid rubber and a tackifier.

In the above-mentioned thermoplastic elastomer, there can be used a styrene group copolymer whose content of styrene is about 40% or less, preferably about 20% or less, and more preferable about 15% or less. The preferred styrene copolymers are SIS (styrene-isoprene-styrene block copolymer), and SEPS (hydrogenated styrene-isoprene block copolymer), for example, available under the tradenames Europrene SOL T190, 192 and 193 from Enichem Corporation, under the tradenames Cariflex TR 1107, 1111, 1112, and 1117 from Shell Chemical Co., Ltd., under the tradenames JSR SIS 5000 and 5002 from Japan Synthetic Rubber Co., Ltd., under the tradenames Quintac 3421, 3422, 3435, and 3450 from Nippon Zeon Co., Ltd., and under the tradenames Cepton 20043 and 2063 from Kuraray Co., Ltd. The other preferred styrene copolymers are SBS (styrene-butadiene-styrene block copolymer), and SEBS (styrene-ethylene-butylene-styrene block copolymer), for example, available under the tradenames Tufprene 315, Asaprene T-420, H Series and M Series of Tuftec from Asahi Chemical Industry Co., Ltd., under the tradenames AR 100, 200, 400 and 500 from Aron Chemical Co., Ltd., under the tradenames Cariflex TR 1101 and 1102, Kraton D1116, 1118, and G1657 from Shell Chemical Co., Ltd. One or a combination of two or more of the above-mentioned substances can be used.

Further, as the elastomer having a low compatibility with the thermoplastic elastomer, polyisobutylene, isobutylene-isoprene rubber, etc. can be used. Preferably the following commerically available products can be used effectively: polyisobutylenes having an average molecular weight of from about 30,000 to about 100,000 such as Himole 4H, 5H and 6H manufactured by Nihon Petrochemical Co., Ltd., Vistanex SQ manufactured by EXXON Chemicals Co., Ltd., and Oppanol manufactured by BASF Corporation. Further, a isobutylene-isoprene rubber such as Butyl 268 manufactured by EXXON Chemicals Co., Ltd., a polyisoprene rubber such as Kuraprene IR-10 manufactured by Kuraray Co., Ltd., JSR 2200 manufactured by Japan Synthetic Rubber Co., Ltd., and Nipol 2200 manufactured by Nippon Zeon Co., Ltd., are used effectively. By the expression "low compatibility" used in the present invention, what is meant is an inter-substance relationship that, in the case where two or more substances are combined, they are not rendered into one individual solid but the respective substances can exist together in a mutually dispersed state.

As the liquid rubber of the softener, there can be used low molecular weight polymers (viscous liquids at normal temperature) such as LIR (liquid isoprene rubber), PB (polybutadiene), etc., fat and oil groups of animals, plants, minerals, etc., and plasticizer groups such as phthalic ester. Preferably, low molecular weight polymers such as liquid polyisoprene, for example, Kuraprene LIR 30 and 50, manufactured by Kuraray Isoprene Chemical Co., Ltd., liquid polybutadiene, for example, POLY BD manufactured by Idemitsu Petrochemical Co., Ltd., Sumika Oil manufactured by Sumitomo Chemical Co., Ltd., Nisseki PB manufactured by Nihon Petrochemical Co., Ltd., POLYOIL manufactured by Nippon Zeon Co., Ltd., JSR CTPB, manufactured by Japan Synthetic Rubber Co., Ltd., liquid, 1,2-polybutadiene, for example, BC manufactured by Nihon Soda Co., Ltd., Nisseki PB manufactured by Nihon Petrochemical Co., Ltd., and liquid styrene-butadiene, for example, POLY-BD manufactured by ARCO Corporation, BUTON manufactured by ESSO Corporation, and further, liquid acrylnitrile-butadiene, liquid polychloroprene, liquid poly (oxypropylene), liquid poly (oxytetramethylene) glycol, liquid polyolefin glycol, etc. can be used. Among them, particularly useful softeners which can soften the styrene group thermoplastic elastomers are liquid polyisoprene having an average molecular weight of from about 2,900 to about 5,000 such as Kuraprene LIR 30 and 50 manufactured by Kuraray Co., Ltd., POLY-BD manufactured by Idemitsu Petrochemical Co. Ltd., POLYOIL manufactured by Nippon Zeon Co., Ltd., the liquid polybutadiene, JSR CTPB manufactured by Japan Synthetic Rubber Co., Ltd., and the liquid styrene-butadiene such as POLY-BD manufactured by ARCO Corporation and BUTON manufactured by ESSO Corporation.

As the tackifier of the softener, resin groups, terpene groups, synthetic petroleum groups, phenol groups, and xylene groups can be used. Substances having a good compatibility with the pressure sensitive adhesive component are desirable. As such substances, there are pointed out, for instance, ARKON P70, and 100 (saturated aliphatic hydrocarbon resins) manufactured by Arakawa Chemical Industries Ltd., Escorez 3108 and 2203 (petroleum resins) manufactured by EXXON Chemicals Co., Ltd., and YS Resin TO-105 (terpene-phenol resin) and Clearon P105 (hydrogenated polyterpene resin) manufactured by Yasuhara Chemical Co., Ltd.

Usable as the water absorbing component are various starches such as flour starch, corn starch, potato starch, etc., mannan such as konjak, various seaweeds such as agar-agar, sodium alginate, etc., various plant mucilages such as tragacanth gum, gum arabic, karaya gum, guar gum, psyllium seed gum, dammar gum, pectin etc., various proteins such as gelatin, collagen, casein, etc., various celluloses such as carboxymethyl cellulose, hydroxyethyl cellulose, methyl cellulose, etc., modified starches such as soluble starch, carboxymethyl starch, dialdehyde starch, etc., synthetic resins such as polyvinyl alcohol, sodium polyacrylate, polyethylene oxide, etc., and copolymers of starches or celluloses and acrylnitrile, acrylic acid, sulfonic acid, vinyl sultanate, etc. The use of the plant mucilages such as tragacanth gum, gum arabic, karaya gum, guar gum, psyllium seed gum, dammar gum, pectin, etc. celluloses such as CMC (carboxymethyl cellulose), HEC (hydroxyethl cellulose), etc., and the copolymers of starches or celluloses and acrylnitrile, acrylic acid, sulfuric acid, vinyl sulfonate, etc. is preferable.

As for the physical properties of an adhesive composition, the following is pointed out: it is desirable that, when the composition is contacted with water at about 37° C., which is approximately the same temperature as the temperature of the human body, the composition should not be disintegrated even if the absorbed amount of sweat oozing out from a patient's skin and/or exudates oozing out from the wound, that is, the amount of such sweat and exudates absorbed by the composition exceeds about 20% of its own weight, and yet, the composition should not swell up to more than about 1.2 times as much as the volume thereof before its absorption of water. The medical adhesive composition should more preferably not be degraded even if the amount of water absorbed exceeds about 50% of its own weight and not swell to more than a volume about 1.2 times as much as the volume thereof before its water absorption.

As for the compounding ratio of the respective components, a suitable compounding ratio between the thermoplastic elastomer and the elastomer having a low compatibility with the thermoplastic elastomer is in the range of from about 8:70 to about 70:15, preferably from about 9:70 to about 56:30. If the compounded amount of the thermoplastic elastomer is too small with respect to the compounded amount of the elastomer having a low compatibility with the thermoplastic elastomer, then the composition is short of elasticity and subject to deformation, cold flowing and cracking, thus ending in an undesirable result. Conversely if the compounded amount of the thermoplastic elastomer is too much, then the elasticity of the composition increases, becomes hard, lowers the water absorbing speed and the amount of water absorbed; and thus, the composition cannot cope with the amount of sweat secreted, thus becoming apt to separate from the patient's skin and, after absorbing water, the composition swells, thus ending in an undesirable result, too.

As the softener, a liquid rubber is compounded at about 30% or more by weight based on the thermoplastic elastomer, whereby the hardness of the thermoplastic elastomer can be lowered to a desirable softness required of an adhesive agent, and thus, a desirable medical adhesive composition can be obtained. If the compounding ratio of the liquid rubber is less than about 30% by weight, then the hardness of the thermoplastic elastomer is too high and thus does not fit well in with the patient's skin; resulting in a composition not desirable as a medical adhesive composition. Further, if only plasticizers and oils and fats are used as the softener, then the thermoplastic elastomer cannot be sufficiently softened, if the softener is compounded in a proportional amount of about 30% or more, it can be mixed temporarily, but the softener rubber and the thermoplastic elastomer are not dissolved in each other, separating from each other with the lapse of time, or even if a mixed composition is obtained, it does not have such physical properties as to ensure that, after its absorption of water, it deforms or swells only a little, thus failing to obtain a desirable medical adhesive composition.

In the present invention, the compounding ratio between the thermoplastic elastomer and the elastomer having a low compatibility with the thermoplastic elastomer, the ratio between the thermoplastic elastomer and the liquid rubber of the softener, and the compounding ratio between the elastomer and the water absorbing component are important factors in achieving the intended effects of the present invention. That is, in order to make a mixture as a desirable medical adhesive component by the use of a thermoplastic elastomer and an elastomer having a low compatibility with the thermoplastic elastomer, it is necessary to select a softener which has a high compatibility with the thermoplastic elastomer and can sufficiently produce physical properties required of a medical adhesive component; desirable in this regard being a liquid rubber softener. In particular, in the case where the thermoplastic elastomer is a styrene copolymer, a high molecular weight low polymer of LIR is preferable as a softener which has a high compatibility with such a styrene copolymer.

Further, for realizing a suitable water absorbing speed and a suitable amount of water absorbed, the amount of the pressure sensitive adhesive component and the amount of the water absorbing component are important factors. The preferred compounding ratio between these components is from about 10 to about 65 W/W %, preferably from about 30 to about 55 W/W %. If this ratio is small, the water absorbing speed is slow, and the amount of water absorbed is small, so that the exudates oozing out from the wound cannot be absorbed, and further, in the case where much sweat exudes, water remains between the patient's skin and the medical composition, which becomes a cause for the separation of the medical composition from the skin. Moreover, in the case where the amount of water absorbing component is large, the medical composition gets hardened and thus ceases to fit in with the movement of the patient's skin or leads to the deformation or breakdown of its shape, thus ending in an undesirable result.

According to the present invention, two elastomers having different characteristics, that is, a thermoplastic elastomer and an elastomer having a low compatibility with the thermoplastic elastomer, are used in combination; these two components are not rendered into one-phase system but a mixture in which the respective components are uniformly dispersed, that is, constitute a sea-island-like structure. Further, the water absorbing component mixed in this sea-island-like structure of the elastomer is more apt to mix with the elastomer having a low compatibility with the thermoplastic elastomer than with the thermoplastic elastomer thus resulting in a state in which a large amount of the water absorbing component is contained in the elastomer component having a low compatibility with the thermoplastic elastomer. Therefore, upon contact with water or exudates, the water absorbing component contained in a large amount in the elastomer having a low compatibility with the thermoplastic elastomer exhibits a high water absorption characteristic. Further, the water or the exudates absorbed diffuse into the adjacent water absorbing component, thus securing the amount of water absorbed. In this case, the thermoplastic elastomer serves as a skeleton and, since this skeleton component and the low compatibility elastomer have an affinity with each other, they are not pushed out, so that only the water absorbing component which has absorbed water is lowered in its affinity with the elastomer and enhanced in its flowability and thus pushed out. Due to this, the adhesive component which retains its shape can keep on holding its adhesive force for adhering to the patient's skin.

An embodiment of the present invention will now be described.

Embodiment 1: about 30 parts by weight of a thermoplastic elastomer SIS ("Europrene SOL T 190" manufactured by EniChem Corporation) and, about 10 parts by weight of polyisobutylene ("Himol" 5II manufactured by Nihon Petroleum Co., Ltd.) and about 10 parts by weight of butyl rubber ("Butyl 268" manufactured by EXXON Chemicals Co., Ltd.) as an elastomer having a low compatibility with the thermoplastic elastomer, and about 20 parts by weight of a liquid rubber LIR ("Kuraprene LIR 30" manufactured by Kuraray Co., Ltd.) were fed into a pressure kneader and sufficiently mixed until a uniform mixture could be obtained. Next, as a tackifier, about 46 parts by weight of a petroleum resin ("ARKON P70" manufactured by Arakaw Chemical Industries Ltd.) and about 26 parts by weight of another petroleum resin ("EK31L" manufactured by Arakawa Chemical Industries Ltd.) were added, and the whole was mixed until a uniform mixture was obtained. Finally, about 18 parts by weight of carboxymethyl cellulose ("CMC1380" manufactured by Daicel Co., Ltd.), about 6 parts by weight of karaya gum, 36 parts by weight of gelatin NC, 10 parts by weight of guarpack PM-1 and about 36 parts by weight of pectin, which were prepared and mixed beforehand as a water absorbing component, and about 15 parts by weight of Nipseal VN-3 as a hydrophobic filler, were added, and the whole was mixed under pressure, whereby an adhesive composition was produced.

Other embodiments of the present invention which were constituted by compounding different components in a manner similar to that of Embodiment 1 and comparative examples which were constituted by the use of the conventional components are shown in Tables 1 to 4 for a comparison between the characteristics thereof:

TABLE 1

| Material | | Embodiment 1 Part Number | % | Embodiment 2 Part Number | % | Embodiment 3 Part Number | % | Embodiment 4 Part Number | % | Embodiment 5 Part Number | % | Embodiment 6 Part Number | % |
|---|---|---|---|---|---|---|---|---|---|---|---|---|---|
| Thermoplastic elastomer | SIS Europrene SOLT19 | 30.0 | 10.2 | | | | | | | | | | |
| | SIS Cariflex TR1107 | | | 120.0 | 24.0 | 64.0 | 12.8 | 105.0 | 21.0 | 105.0 | 20.9 | 85.7 | 17.1 |
| Low compatibility elastomer | Polyisobutylene Himol 4H | | | 60.0 | 12.0 | 32.0 | 6.4 | 30.0 | 6.0 | | | | |
| | Polyisobutylene Himol 5H | 40.0 | 13.6 | | | | | | | | | | |
| | Polyisobutylene Himol 6H | | | | | | | | | 19.0 | 3.8 | 18.1 | 3.6 |
| | Butyl 268 | 10.0 | 3.4 | | | | | | | 20.0 | 4.0 | 19.0 | 3.8 |
| Softener | LIR Kuraprene LIR 30 | 20.0 | 6.8 | 75.0 | 15.0 | 128.0 | 25.6 | 90.0 | 18.0 | 90.0 | 17.9 | 100.0 | 19.9 |
| | LIR Polybutene HV 1900 Liquid paraffin Mineral Oil | | | | | | | | | 6.0 | 1.2 | 5.7 | 1.1 |
| Tackifier | Petroleum Group resin ARKON P70 | 46.0 | 15.7 | 45.0 | 9.0 | 64.0 | 12.8 | 60.0 | 12.0 | 40.0 | 8.0 | 47.6 | 9.5 |
| | EK31L | 26.0 | 8.9 | | | | | | | 20.0 | 4.0 | 23.8 | 4.7 |
| Water absorbing component | CMC CMC 1190 | | | | | | | | | | | | |
| | CMC CMC 1380 | 18.0 | 6.1 | 102.0 | 20.4 | 102.0 | 20.4 | 102.0 | 20.4 | 100.2 | 20.0 | 100.2 | 20.0 |

TABLE 1-continued

| Material | | Embodiment 1 Part Number | % | Embodiment 2 Part Number | % | Embodiment 3 Part Number | % | Embodiment 4 Part Number | % | Embodiment 5 Part Number | % | Embodiment 6 Part Number | % |
|---|---|---|---|---|---|---|---|---|---|---|---|---|---|
| | Karaya gum #150 | 6.0 | 2.1 | 60.3 | 12.1 | 60.3 | 12.1 | 60.3 | 12.1 | 59.2 | 11.8 | 59.2 | 11.8 |
| | Gelatin NC | 36.0 | 12.3 | 15.4 | 3.1 | 15.4 | 3.1 | 15.4 | 3.1 | 15.2 | 3.0 | 15.2 | 3.0 |
| | Guar Gum | 10.0 | 3.4 | 15.4 | 3.1 | 15.4 | 3.1 | 15.4 | 3.1 | 15.2 | 3.0 | 15.2 | 3.0 |
| | Pectin | 36.0 | 12.3 | | | | | | | | | | |
| Hydrophobic component | Nipseal VN-3 | 15.0 | 5.1 | 6.6 | 1.3 | 6.6 | 1.3 | 6.6 | 1.3 | 12.0 | 2.4 | 12.0 | 2.4 |

TABLE 2

| Material | | Embodiment 7 Part Number | % | Embodiment 8 Part Number | % | Embodiment 9 Part Number | % | Embodiment 10 Part Number | % | Embodiment 11 Part Number | % | Embodiment 12 Part Number | % |
|---|---|---|---|---|---|---|---|---|---|---|---|---|---|
| Thermoplastic elastomer | SIS Europrene SOLT19 | | | 49.5 | 9.9 | 52.5 | 10.4 | | | | | 57.7 | 11.4 |
| | SIS Cariflex TR1107 | 66.0 | 13.2 | | | | | 57.7 | 11.4 | 57.7 | 11.4 | | |
| Low compatibility elastomer | Polyisobutylene Himol 4H | | | | | | | | | | | | |
| | Polyisobutylene Himol 5H | | | | | | | | | | | | |
| | Polyisobutylene Himol 6H | 30.4 | 6.1 | 30.4 | 6.1 | 29.7 | 5.9 | 23.0 | 4.5 | 27.4 | 5.4 | 51.8 | 10.2 |
| | Butyl 268 | 32.0 | 6.4 | 32.0 | 6.4 | 37.1 | 7.3 | 28.8 | 5.7 | 28.8 | 5.7 | 13.0 | 2.6 |
| Softener | LIR Kuraprene LIR 30 | 99.0 | 19.8 | 115.0 | 23.0 | 97.5 | 19.2 | 107.2 | 21.1 | 107.2 | 21.1 | 107.2 | 21.1 |
| | LIR Polybutene HV 1900 | 9.6 | 1.9 | 9.6 | 1.9 | 16.7 | 3.3 | 13.0 | 2.6 | 8.6 | 1.7 | | |
| | Liquid paraffin Mineral Oil | | | | | | | | | | | | |
| Tackifier | Petroleum Group resin ARKON P70 | 42.0 | 8.4 | 42.0 | 8.4 | 42.8 | 8.4 | 45.6 | 9.0 | 45.6 | 9.0 | 45.6 | 9.0 |
| | Petroleum Group resin EK31L | 21.0 | 4.2 | 21.0 | 4.2 | 23.7 | 4.7 | 24.6 | 4.9 | 24.6 | 4.9 | 24.6 | 4.9 |
| Water absorbing component | CMC CMC 1190 | | | | | | | | | | | | |
| | CMC CMC 1380 | 98.5 | 19.7 | 98.5 | 19.7 | 98.5 | 19.4 | 98.5 | 19.4 | 98.5 | 19.4 | 98.5 | 19.4 |
| | Karaya gum #150 | 59.2 | 11.8 | 59.2 | 11.8 | 59.2 | 11.7 | 59.2 | 11.7 | 59.2 | 11.7 | 59.2 | 11.7 |
| | Gelatin NC | 15.2 | 3.0 | 15.2 | 3.0 | 15.2 | 3.0 | 15.2 | 3.0 | 15.2 | 3.0 | | |
| | Guar Gum | 15.2 | 3.0 | 15.2 | 3.0 | 15.2 | 3.0 | 15.2 | 3.0 | 15.2 | 3.0 | 15.2 | 3.0 |
| | Pectin | | | | | 12.0 | 2.4 | 12.0 | 2.4 | 12.0 | 2.4 | 12.0 | 2.4 |
| Hydrophobic component | Nipseal VN-3 | 12.0 | 2.4 | 12.0 | 2.4 | 6.6 | 1.3 | 6.6 | 1.3 | 6.6 | 1.3 | 6.6 | 1.3 |

TABLE 3

| Material | | Comparative Example 1 Part Number | % | Comparative Example 2 Part Number | % | Comparative Example 3 Part Number | % | Comparative Example 4 Part Number | % | Comparative Example 5 Part Number | % | Comparative Example 6 Part Number | % |
|---|---|---|---|---|---|---|---|---|---|---|---|---|---|
| Thermoplastic elastomer | SIS Europrene SOLT19 | | | | | | | | | | | 70.0 | 4.1 |
| | SIS Cariflex TR1107 | 72.5 | 14.5 | 130.5 | 26.1 | 145.0 | 29.0 | 130.5 | 26.1 | 112.5 | 32.5 | | |

TABLE 3-continued

| | | Part Number | % | Part Number | % | Part Number | % | Part Number | % | Part Number | % | Part Number | % |
|---|---|---|---|---|---|---|---|---|---|---|---|---|---|
| Low compatibility elastomer | Polyisobutylene Himol 4H | | | 130.5 | 26.1 | 48.3 | 9.7 | 72.5 | 14.5 | 62.5 | 18.1 | | |
| | Polyisobutylene Himol 5H | 145.0 | 29.0 | | | | | | | | | | |
| | Polyisobutylene Himol 6H | | | | | | | | | | | 20.0 | 11.6 |
| | Butyl 268 | | | | | | | | | | | 5.0 | 2.9 |
| Softener | LIR Kuraprene LIR 30 | | | | | | | | | | | 18.0 | 10.5 |
| | LIR Polybutene HV 1900 | | | | | | | 29.0 | 5.8 | | | | |
| | Liquid paraffin | | | | | 32.2 | 6.4 | | | 25.0 | 7.2 | | |
| | Mineral Oil | | | | | | | | | 50.0 | 14.5 | | |
| Tackifier | Petroleum Group resin ARKON P70 | 72.5 | 14.5 | 29.0 | 5.8 | 64.4 | 12.9 | 58.0 | 11.6 | 25.0 | 7.2 | 50.0 | 29.1 |
| | Petroleum Group resin EK31L | | | | | | | | | | | | |
| Water absorbing component | CMC CMC 1190 | | | 107.2 | 21.4 | 107.2 | 21.5 | 107.2 | 21.4 | 40.0 | 11.6 | 32.0 | 18.6 |
| | CMC CMC 1380 | 107.2 | 21.5 | | | | | | | | | | |
| | Karaya gum #150 | 63.3 | 12.7 | 63.3 | 12.7 | | | | | 25.0 | 7.2 | 18.0 | 10.5 |
| | Gelatin NC | 16.2 | 3.2 | 16.2 | 3.2 | 63.3 | 12.7 | 63.3 | 12.7 | 6.0 | 1.7 | 17.0 | 9.9 |
| | Guar Gum | 16.2 | 3.2 | 16.2 | 3.2 | 16.2 | 3.2 | 16.2 | 3.2 | | | | |
| | Pectin | | | | | 16.2 | 3.2 | 16.2 | 3.2 | | | | |
| Hydrophobic component | Nipseal VN-3 | 6.9 | 1.4 | 6.9 | 1.4 | 6.9 | 1.4 | 6.9 | 1.4 | | | 5.0 | 2.9 |

| | | Comparative Example 7 | | Comparative Example 8 | | Comparative Example 9 | | Comparative Example 10 | | Comparative Example 11 | |
|---|---|---|---|---|---|---|---|---|---|---|---|
| Material | | Part Number | % | Part Number | % | Part Number | % | Part Number | % | Part Number | % |
| Thermoplastic elastomer | SIS Europrene SOLT19 | 15.0 | 5.9 | 10.0 | 5.0 | | | | | | |
| | SIS Cariflex TR1107 | | | | | | | | | | |
| Low compatibility elastomer | Polyisobutylene Himol 4H | 24.0 | 9.5 | | | 32.0 | 14.7 | 70.0 | 31.0 | | |
| | Polyisobutylene Himol 5H | | | | | 48.0 | 22.0 | 20.0 | 8.9 | 50.0 | 21.3 |
| | Polyisobutylene Himol 6H | | | 20.0 | 9.9 | | | | | | |
| | Butyl 268 | 6.0 | 2.4 | 5.0 | 2.5 | | | 10.0 | 4.4 | | |
| Softener | LIR Kuraprene LIR 30 | 15.0 | 5.9 | 15.0 | 7.4 | | | | | | |
| | LIR Polybutene HV 1900 | | | | | | | | | | |
| | LIR Polybutene HV 15 | | | | | | | | | 25.4 | 10.8 |
| | Liquid paraffin | | | | | | | | | | |
| | Mineral Oil | | | | | | | | | | |
| Tackifier | Petroleum Group resin ARKON P70 | 46.0 | 18.2 | 50.0 | 24.8 | | | | | | |
| | Petroleum Group resin EK31L | 26.0 | 10.3 | | | | | | | | |
| | Petroleum Group resin Escorex #10 | | | | | 20.0 | 9.2 | | | 50.0 | 21.3 |
| Water absorbing component | CMC CMC 1190 | | | 32.0 | 15.8 | 5.0 | 2.3 | 62.7 | 27.8 | 20.3 | 8.7 |
| | CMC CMC 1380 | 18.0 | 7.1 | | | | | | | | |
| | Karaya gum | 6.0 | 2.4 | 42.0 | 20.8 | 39.4 | 18.1 | 36.7 | 16.3 | 48.3 | 20.6 |

TABLE 3-continued

|  | #150 |  |  |  |  |  |  |  |  |  |  |
|---|---|---|---|---|---|---|---|---|---|---|---|
|  | Gelatin NC | 36.0 | 14.2 | 23.0 | 11.4 | 33.3 | 18.3 | 9.4 | 4.2 | 30.3 | 12.9 |
|  | Guar Gum | 10.0 | 4.0 |  |  | 33.3 | 15.3 | 9.4 | 4.2 | 5.0 | 2.1 |
|  | Pectin | 36.0 | 14.2 |  |  |  |  |  |  |  |  |
| Hydrophobic component | Nipseal VN-3 | 15.0 | 5.9 | 5.0 | 2.5 | 6.7 | 3.1 | 7.3 | 3.2 | 5.0 | 2.1 |

The specimens were prepared to be measured as follows: after the embodiments and the comparative examples were put into a thermostatic chamber at from about 60° to about 120° C. for softening thereof, the compositions were each held between two release papers for prevention of the sticking thereof to other things and rendered into a sheet about 2 mm thick by the use of pressure rollers. Next, from each of the thus formed sheets, two specimens (a) and (b) were made:
  (a) The release paper on one side surface of the sheet about 2 mm thick was removed, and, onto the thus exposed surface of the sheet, a polyurethane film 0.03 mm thick was stuck and then cut to a width of 100 mm and a length of 100 mm, thus forming Specimen 1.
  (b) Each said sheet about 2 mm thick was cut into a round shape having a diameter of 30 mm; and five of the thus shaped sheets were put one upon another to a thickness of about 10 mm, removing the release papers, whereby Specimen 2 was formed.

Measurement of the initial tack: The initial tack of Specimen 1 was measured in terms of the Picmatack value by the use of a Picmatack Tester (manufactured by Toyo Sciki Co., Ltd.) at a room temperature of 20° C. The measuring principle of this Picmatack is that an aluminum disc 50 mm in diameter and 14 mm in thickness is pressed against a specimen under a load of 500 g for 2 seconds and then pulled up at a pull-up speed of 30 mm/sec, in which case the force required for tearing the disc off the specimen is the picmatack value.

Hardness measurement: Specimen 2 was left to stand in the thermoplastic chamber at 37° C. for three hours, and then, after a load was applied to the Specimen 2 by the use of a JIS KK2207 "Petroleum Asphalt" (penetration test method) tester for 5 seconds, the penetration value was measured, and the value resulting from increasing this value by ten times was used as data. As the needle, a conical needle having a diameter of 23.96 mm and a height of 43.83 mm was used.

Cold flow measurement: Specimen 2 which was left to stand in the thermoplastic chamber at 37° C. was placed on a flat plate, and then a load of 500 g which had a bottom surface larger than the surface size thereof was applied to Specimen 2, and, after 24 hours, the load was removed. The length of the overflowing portion of Specimen 2 was measured, thus obtaining the percentages of deformation of Specimen 2 with respect to the shape thereof before application of the load.

Water absorption measurement: The release paper was peeled off from the one side surface of Specimen 2, in which state the weight thereof was measured, and then, after it was immersed into a 0.9% saline solution (physiologic saline solution), it was put in the thermostatic chamber at 37° C. and taken out after 3 hours, after 6 hours, and after 24 hours to measure the weight of the specimen each time, so that, from the values thus obtained, the weight of the physiologic saline solution absorbed was calculated with respect to the weight thereof before the above-mentioned treatment was performed, thus obtaining the water absorption rate.

Swell measurement: The release paper was peeled off one side surface of Specimen 2, in which state the diameter thereof was accurately measured, and, after immersed into a 0.9% saline solution (physiologic saline solution) at 31° C., Specimen 2 was put and left in the thermostatic chamber at 37° C.; and after 24 hours, Specimen 2 was taken out, and the diameter thereof was measured, so that, from the value thus obtained the length of the swollen portion was measured with respect to the diameter thereof before it swelled, thus obtaining the percentage of swelling.

Evaluation of the disintegration: The release paper was peeled off one side surface of Specimen 2, and, after being immersed into a 0.9% saline solution (physiologic saline solution) at 37° C., Specimen 1 was put and kept in the thermostatic chamber at 37° C., taken out after 24 hours, violently shaken in a purified water at 37° C. again, and pulled out to observe the shape thereof, thus evaluating the degree of disintegration thereof.

The results of the measurements made of Embodiments 1 to 12 and Comparative Examples 1 to 11 by the use of the measuring method mentioned above are as follows: The initial tack values of the Embodiments thus measured were from about 0.600 to about 1.5000 kgf, and the average value was was 1.250 kgf. The measured hardness values of the Embodiment were from about 10 to about 40, and the average value was about 25. The percentages of deformation obtained through the measurements made on the Embodiments were from about 0 to about 5 mm, and the average value was about 2.5 mm; the Embodiments were also flexible and hard to be made to cold flow. The water absorption rate, which is a water absorption characteristic, of the Embodiments was from about 50 to about 500% after 3 hours (of their immersion in water), from about 150 to about 410% after 6 hours, and from about 250 to about 1200% after 24 hours. The degree of swelling of the Embodiments measured for detection of the shape change thereof after their absorption of water was from about 1.06 times to about 1.19 times, and the average value was about 1.09 times. According to these evaluation results pertaining to the disintegration of the Embodiments, the embodiments were not disintegrated at all, but, in connection with the above-mentioned water absorption rate measurement, it was observed that, in the case of only those compositions which decreased in weight when they were immersed into the saline solution for many hours, the water soluble substances cluted from their portions highly contacted with the physiologic saline solution, leaving the network structure of the elastomer component.

On the other hand, the values obtained through the measurements made on the initial tack of the Comparative Examples were from about 0.580 to about 1.410 kgf. The values obtained through the hardness measurements made on the Comparative Examples were from about 7 to about 45. The percentages of deformation obtained through the cold flow measurements made on the Comparative Examples were from about 0 to about 8 mm; those compositions which had flexibility were liable to cold flow, while conversely those compositions which were high in hardness were not subjected to cold flow. The water absorption rate, which is a water absorption characteristic, of the Comparative Examples was from about 65 to about 230% after 3 hours, from about 160 to about 350% after 6 hours, and from about 210 to about 580% after 24 hours. The values obtained through the measurements made on the degrees of swelling (being an indication of the shape change) of the Comparative Examples after their absorption of water were from about 0.01 time to about 1.53 times; from these evaluation results pertaining to the disintegration, it was observed that those compositions which had high water absorption rates disintegrated or deformed to lose their original shapes completely or, conversely, the water soluble substances in the portions thereof contacted with the physiologic saline solution swelled to spread the elastomer component, whereby the specimens of the Comparative Examples were swollen in the length direction and the thickness direction thereof.

Thus there has been shown and described several embodiments of a novel medical adhesive composition which fulfill all of the objects and advantages set forth above. It will be apparent to those skilled in the art, however, that many changes, modifications, variations and other uses and applications for the subject invention are possible. All such changes, modifications, variations and other uses and applications which do not depart from the spirit and scope of the invention are deemed to be covered by the invention which is limited only by the claims which follow.

What is claimed is:

1. Medical adhesive composition comprising, as essential components, a pressure sensitive adhesive component and a water absorbing component, the pressure sensitive adhesive component consisting of an elastomer comprised of a thermoplastic elastomer and an elastomer having a low compatibility with the thermoplastic elastomer, and a softner containing at least a liquid rubber and a tackifier, wherein the thermoplastic elastomer of the pressure sensitive adhesive component is a styrene copolymer, in which the amount of bound styrene is about 40% by weight or less, the liquid rubber of the softener is contained in a proportional amount of about 30% by weight or more based on the thermoplastic component and the elastomer having a low compatibility with said thermoplastic elastomer is selected from the group consisting of one or a combination of both of PIB (polyisobutylene) and IIR (isobutylene-isoprene-rubber).

2. Medical adhesive composition according to claim 1, wherein the thermoplastic elastomer and the elastomer having a low compatibility with the thermoplastic elastomer are mixed so as to exist together as distinct substances in a mutually dispersed multi-phase state.

3. Medical adhesive composition according to claim 2, wherein the styrene copolymer is selected from the group consisting of one or a combination of two or more of SIS (styrene-isoprene-styrene block copolymer), SBS (styrene-butadiene-styrene block copolymer), SEBS (styrene-ethylene-butylene-styrene block copolymer), and SEPS (hydrogenated styrene-isoprene block copolymer).

4. Medical adhesive composition according to claim 1, wherein the compounding ratio between the thermoplastic elastomer and the elastomer having a low compatibility with the thermoplastic elastomer of the pressure sensitive adhesive component is between about 8:70 and about 70:15.

5. Medical adhesive composition according to claim 1, wherein said composition comprises from about 2 to about 35 wt. % of the thermoplastic elastomer component, from about 0 to about 44 wt. % of PIB and from about 0 to about 22 wt. % of the IIR as the elastomer having a low compatibility with the thermoplastic elastomer, from about 4 to about 36 wt. % of the LIR and from about 0 to about 4 wt. % of polybutene as the softener, from about 5 to about 53 wt. % of the tackifier, and from about 10 to about 60 wt. % of one or more of karaya gum, pectin, gelatin, guar gum, locust bean gum, and a carboxymethycellulose derivative and from about 0 to about 20 wt. % of silica as the water absorbing component.

6. Medical adhesive composition comprising, as essential components, a pressure sensitive adhesive component and a water absorbing component the pressure sensitive adhesive component having a multi-phase matrix structure consisting of an elastomer comprising a thermoplastic elastomer and an elastomer having a low compatibility with the thermoplastic elastomer, a softener containing at least a liquid rubber in an amount equal to at least about 30% by weight of the thermoplastic elastomer component and a tackifier, wherein the amount of water absorbed by said composition when it is left to stand in water at 37° C. for 24 hours is at least about 20% based on said composition's own weight, the swelling thereof is less than about 1.2 times as high as that before its absorption of water and said pressure sensitive adhesive component with the matrix structure does not disintegrate, even if the water absorbing component is pushed out.

* * * * *

UNITED STATES PATENT AND TRADEMARK OFFICE
CERTIFICATE OF CORRECTION

PATENT NO. : 5,827,528
DATED : October 27, 1998
INVENTOR(S) : Takabumi Kubo and Igarashi Masatoshi It is certified that error appears in the above-identified patent and that said Letters Patent is hereby corrected as shown below:

Column 10,

Table 2, Embodiment 12 Column, Gelatin NC Row, insert 15.2 under Part Number column, and 3.0 under % column.

Signed and Sealed this

Sixteenth Day of March, 1999

Attest:

Attesting Officer

Q. TODD DICKINSON

Acting Commissioner of Patents and Trademarks